(12) United States Patent
Puah et al.

(10) Patent No.: US 9,932,275 B2
(45) Date of Patent: Apr. 3, 2018

(54) TREATMENT OF ORGANIC WASTE

(71) Applicant: Biomax Holdings PTE LTD, Singapore (SG)

(72) Inventors: Chum Mok Puah, Singapore (SG); Eng Tong Sim, Singapore (SG); Siok Lui Chua, Singapore (SG)

(73) Assignee: Biomax Holdings PTE LTD, Singapore (SG)

( * ) Notice: Subject to any disclaimer, the term of this patent is extended or adjusted under 35 U.S.C. 154(b) by 194 days.

(21) Appl. No.: 14/269,822

(22) Filed: May 5, 2014

(65) Prior Publication Data

US 2014/0318201 A1 Oct. 30, 2014

Related U.S. Application Data

(62) Division of application No. 13/636,320, filed as application No. PCT/SG2011/000113 on Mar. 23, 2011, now abandoned.

(30) Foreign Application Priority Data

Mar. 23, 2010 (GB) .................................. 1004820.5

(51) Int. Cl.
| | |
|---|---|
| *C05B 15/00* | (2006.01) |
| *C02F 3/34* | (2006.01) |
| *C05F 17/00* | (2006.01) |
| *C12R 1/225* | (2006.01) |
| *C12R 1/38* | (2006.01) |
| *C12R 1/07* | (2006.01) |

(52) U.S. Cl.
CPC ................ *C05B 15/00* (2013.01); *C02F 3/34* (2013.01); *C05F 17/0036* (2013.01); *C12R 1/07* (2013.01); *C12R 1/225* (2013.01); *C12R 1/38* (2013.01); *Y02P 20/145* (2015.11); *Y02W 10/37* (2015.05); *Y02W 30/43* (2015.05)

(58) Field of Classification Search
CPC ........ C05B 15/00; C02F 3/34; C05F 17/0036; Y02W 10/37; Y02W 30/43; Y02P 20/145; C12R 1/07; C12R 1/38; C12R 1/225
USPC ...................................................... 435/262.5
See application file for complete search history.

(56) References Cited

U.S. PATENT DOCUMENTS

| | | | | |
|---|---|---|---|---|
| 3,356,609 | A * | 12/1967 | Bruemmer ............ | C02F 3/1215 210/610 |
| 6,197,081 | B1 * | 3/2001 | Schmidt .................. | A61L 11/00 588/249 |
| 6,365,384 | B1 | 4/2002 | Iijima | |
| 6,383,246 | B1 * | 5/2002 | Konishi ................... | C05F 11/00 71/13 |
| 6,447,568 | B1 * | 9/2002 | Shiiba .................. | C05F 17/0036 71/11 |
| 7,678,268 | B2 * | 3/2010 | Smith ..................... | C02F 1/283 210/189 |
| 2004/0115090 | A1 * | 6/2004 | Andersson .............. | A61L 11/00 422/1 |
| 2007/0060477 | A1 * | 3/2007 | Pedersen ............... | A23L 1/0345 504/100 |
| 2009/0120147 | A1 * | 5/2009 | Blais ....................... | A01N 63/00 71/8 |
| 2009/0126432 | A1 * | 5/2009 | Porubcan ................. | C05B 1/00 71/6 |

FOREIGN PATENT DOCUMENTS

| | | |
|---|---|---|
| CN | 1482108 A | 3/2004 |
| CN | 1861199 * | 11/2006 |
| CN | 1861199 MT * | 11/2006 |
| JP | H0672788 A | 3/1994 |
| JP | H0912387 A | 1/1997 |
| JP | H09206066 A | 8/1997 |
| JP | H10152386 A | 6/1998 |
| JP | H10251087 A | 9/1998 |
| JP | 2000354852 A | 12/2000 |
| JP | 2001354487 A | 12/2001 |
| JP | 2002058471 A | 2/2002 |
| JP | 2003009848 A | 1/2003 |
| JP | 2003094095 A | 4/2003 |
| JP | 2004269351 A | 9/2004 |
| JP | 2005021010 A | 1/2005 |
| JP | 2005161296 A | 6/2005 |
| JP | 2009278895 A | 12/2009 |
| JP | 2010001169 A | 1/2010 |

OTHER PUBLICATIONS

Ryckeboer et al. (2003). A survey of bacteria and fungi occurring during composting and self-heating processes. Annals of Microbiology, v53(4), p. 349-410.*

Ichida et al. (2001). Bacterial inoculum enhances keratin degradation and biofilm formation in poultry compost. Journal of Microbiological Methods, v47, p. 199-208.*

Office Action issued in corresponding Japanese Application No. 2013-501216 with English translation dated Mar. 10, 2015 (9 pages).

* cited by examiner

*Primary Examiner* — Sean C. Barron
(74) *Attorney, Agent, or Firm* — Osha Liang LLP (57) ABSTRACT

The present invention relates to a process for treating organic waste, which comprises the step of contacting an organic waste with one or more microorganisms from at least three of the following microorganism species: *Bacillus* sp. microorganisms, *Pseudomonas* sp. microorganisms, *Bifidobacterium* sp. microorganisms and *Lactobacillus* sp. microorganisms, the contacting being undertaken under conditions to at least partly convert the organic waste to organic fertilizer.

20 Claims, 1 Drawing Sheet

TREATMENT OF ORGANIC WASTE

CROSS REFERENCE TO RELATED APPLICATIONS

This Application is a divisional application and claims benefit under 35 U.S.C. § 120 to U.S. patent application Ser. No. 13/636,320, filed Sep. 20, 2012, which is a 371 national stage filing of international application PCT/SG2011/000113, filed Mar. 23, 2011 which claims the benefit under 35 U.S.C. § 119(b) of Great Britain Patent Application Serial No. 1004820.5 filed Mar. 23, 2010. All of these applications are incorporated by reference in their entirety herein.

TECHNICAL FIELD

The present invention generally relates to a process for treating organic waste. The present invention also relates to a composition, a system and a kit for treating organic waste.

BACKGROUND

Large amounts of organic waste are generated annually from agricultural plantations, animal farms, mills, food processing plants and industrial plants. The amount of organic waste generated has been increasing each year as the agro-food industries expand. Consequently, the disposal of these wastes has been a major concern in recent years.

The conventional methods of disposal of organic waste are landfilling and incineration. Landfills require extensive areas and are both unsanitary and unsightly. Furthermore, landfills create problems such as the leaching of harmful chemicals into the soil, contaminating ground water, and causing loss of essential nutrients into the soil. Incineration is expensive, energy-intensive and creates environmental problems. For example, Malaysia, which has over 2.65 million hectares of oil palm plantations and, can generate 90% total biomass of waste annually of all harvested materials, has prohibited open burning of organic waste to prevent air pollution. The European Union has also mandated a general ban on landfilling of organic waste in 2005.

Biological treatment of organic waste has been applied in an attempt to address the problem of organic waste disposal. Biological treatment of organic waste can convert organic waste into harmless and value-added products. Biological treatment methods use naturally-occurring microorganisms to degrade complex hydrocarbon-contaminated waste into simpler low-carbon, non-toxic residues via fermentation. Desirably, the product residues of biological treatment methods are typically harmless and therefore there is typically no requirement for any post-process treatment, storage or discharge. However, the natural composting of organic waste, such as agricultural waste and animal manure, can take up to six months to mature and achieve a carbon to nitrogen ratio (C:N ratio) that is suitable for use as fertilizer, and typically results in a product with relatively low NPK values (typically less than 2) and is therefore less useful and less valuable as an organic fertilizer.

There is a need to provide a process for the treatment of organic waste that overcomes, or at least ameliorates, one or more of the disadvantages described above.

There is a need to provide an efficient, simple, cost-effective, and environmentally friendly process for treatment of organic waste to reduce the C:N ratio of the organic waste and produce organic fertilizers of high NPK values.

SUMMARY

Disclosed is a process for treating organic waste, the process comprising the step of contacting an organic waste with at least one of the following microorganisms: *Bacillus* sp. microorganisms, *Pseudomonas* sp. microorganisms, *Bifidobacterium* sp. microorganisms and *Lactobacillus* sp. microorganisms, the contacting being undertaken under conditions to at least partly convert the organic waste to organic fertilizer.

According to a first aspect, there is provided a process for treating organic waste, the process comprising the step of contacting an organic waste with one or more microorganisms from at least three of the following microorganism species: *Bacillus* sp. microorganisms, *Pseudomonas* sp. microorganisms, *Bifidobacterium* sp. microorganisms and *Lactobacillus* sp. microorganisms, the contacting being undertaken under conditions to at least partly convert the organic waste to organic fertilizer.

In some embodiments, the disclosed process comprises the step of contacting an organic waste with at least two, at least three, at least four, at least five, at least six, at least seven, at least eight, at least nine, or more of the following microorganisms: *Bacillus* sp. microorganisms, *Pseudomonas* sp. microorganisms, *Bifidobacterium* sp. microorganisms and *Lactobacillus* sp. microorganisms.

In one embodiment, the disclosed process further comprises the step of contacting the organic waste with one or more microorganisms selected from the group consisting of *Streptomyces* sp. microorganisms, and *Corynebacterium* sp. microorganisms.

In some embodiments, the disclosed process further comprises the step of contacting the organic waste with one, two, three, four, five, six, seven, eight, nine, or more microorganisms selected from the group consisting of *Streptomyces* sp. microorganisms, and *Corynebacterium* sp. microorganisms.

In some embodiments, a specialty blend of the microorganism species may be used to promote conversion of the organic waste to organic fertilizer. Additionally, the organic waste may be supplemented with additives and nutrients to further promote the conversion.

Advantageously, the process parameters and the consortium of microorganism species may be tailored for treatment of different compositions of waste. More advantageously, the tailored selection of process parameters and consortium of microorganism species accelerates the treatment process to reduce the treatment time from several months to one to several days. Advantageously, the tailored selection of process parameters and consortium of microorganism species accelerates the treatment process such that the initial C:N ratio of the organic waste may be substantially reduced to a range suitable for use as organic fertilizer within one to several days.

Also disclosed is the use of at least one of the following microorganisms: *Bacillus* sp. microorganisms, *Pseudomonas* sp. microorganisms, *Bifidobacterium* sp. microorganisms and *Lactobacillus* sp. microorganisms, for treating an organic waste to produce organic fertilizer, increase the NPK value of an organic fertilizer, increase the potassium value of an organic fertilizer, reduce odour of an organic waste, prevent leaching of nutrients from organic waste, or reduce waste accumulation.

According to a second aspect, there is provided the use of one or more microorganisms from at least three of the following microorganism species: *Bacillus* sp. microorganisms, *Pseudomonas* sp. microorganisms, *Bifidobacterium* sp. microorganisms and *Lactobacillus* sp. microorganisms, for treating an organic waste to produce organic fertilizer, increase the NPK value of an organic fertilizer, increase the potassium value of an organic fertilizer, reduce odour of an organic waste, prevent leaching of nutrients from organic waste, or reduce waste accumulation.

Further disclosed is a composition for treating an organic waste, the composition comprising at least one of the following microorganisms: *Bacillus* sp. microorganisms, *Pseudomonas* sp. microorganisms, *Bifidobacterium* sp. microorganisms and *Lactobacillus* sp. microorganisms.

According to a third aspect, there is provided a composition for treating an organic waste, the composition comprising one or more microorganisms from at least three of the following microorganism species: *Bacillus* sp. microorganisms, *Pseudomonas* sp. microorganisms, *Bifidobacterium* sp. microorganisms and *Lactobacillus* sp. microorganisms.

In one embodiment, the composition is a solution.

In one embodiment, the composition is a powder.

According to a fourth aspect, there is provided an organic fertilizer comprising an organic waste and a composition as defined above.

Also disclosed is a kit for use in treating an organic waste, the kit comprising:
(a) a composition comprising at least one of *Bacillus* sp. microorganisms, *Pseudomonas* sp. microorganisms, *Bifidobacterium* sp. microorganisms, and *Lactobacillus* sp. microorganisms, and
(b) instructions for contacting the composition with an organic waste under conditions to at least partly convert the organic waste to organic fertilizer.

According to a fifth aspect, there is provided a kit for use in treating an organic waste, the kit comprising:
(a) a composition comprising one or more microorganisms from at least three of the following microorganism species: *Bacillus* sp. microorganisms, *Pseudomonas* sp. microorganisms, *Bifidobacterium* sp. microorganisms, and *Lactobacillus* sp. microorganisms, and
(b) instructions for contacting the composition with an organic waste under conditions to at least partly convert the organic waste to organic fertilizer.

Disclosed is a system for treating an organic waste comprising:
(a) stirring means for mixing an organic waste and a composition as defined above in a treatment zone, wherein the stirring means comprise at least two arms located at different heights along the longitudinal, axis of the treatment zone; and
(b) heating means for heating the organic waste; wherein the heating means is configured to heat the organic waste to sequentially decontaminate and at least partly treat the organic waste.

In one embodiment, the at least two arms of the stirring means extend radially from the center of the treatment zone. Advantageously, the location of the at least two arms of the stirring means at different heights along the longitudinal axis of, and extending radially from the center of the treatment zone promotes mixing of the organic waste and the composition to enhance treatment of the organic waste. In particular, the location of the at least two arms of the stirring means at different heights along the longitudinal axis of the treatment zone ensures that the organic waste and composition as defined above disposed at the bottom of the treatment zone are rapidly and well mixed with the organic waste and composition as defined above disposed at the top of the treatment zone, and that the mixture can achieve the desired temperature, moisture content and aeration level.

DEFINITIONS

The following words and terms used herein shall have the meaning indicated:

The term "organic waste" as used herein refers to carbon-containing substances that are of biological origin, and may be derived from living or formerly living organisms.

The terms "treat," "treatment," and grammatical variants thereof, when used herein with reference to an organic waste refers to contact of the organic waste with a disclosed composition which results in degradation or conversion of the chemical compounds contained within the organic waste. For example, the treatment may involve degradation of the chemical compounds so as to neutralize odorous compounds contained therein and render the organic waste odorless, or conversion of the carbon-compounds or nitrogen fixation so as to increase the nutrient level of the organic waste. The degradation or conversion may be, for example, effected by the enzymes that are secreted by the one or more microorganisms in the disclosed composition. Exemplary enzymes include, but are not limited to, cellulases, amylases, xylanases, galactanases, mannanases, arabanases, β-1,3-1, 4-glucanases, glucosidases, xylosidases, lipases, hemicellulases, pectinases, proteases, pectin esterases, and the like.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DISCLOSURE OF OPTIONAL EMBODIMENTS

Exemplary, non-limiting embodiments of a process, composition, kit and system for treating organic waste, will now be disclosed.

There is provided a process for treating organic waste, the process comprising the step of contacting an organic waste with one or more microorganisms from at least three of the following microorganism species: *Bacillus* sp. microorganisms, *Pseudomonas* sp. microorganisms, *Bifidobacterium* sp. microorganisms and *Lactobacillus* sp. microorganisms, the contacting being undertaken under conditions to at least partly convert the organic waste to organic fertilizer.

Organic waste that may be treated using the disclosed process, composition, kit and system include, but are not limited to agricultural waste, food waste, organic refuse, mill effluent, municipal waste, sewage, sludge, animal waste, and industrial waste. Exemplary agricultural wastes include, but are not limited to, oil palm empty fruit bunch (EFB), palm decanter cake slurry, olive husk, corn cob, coffee bean husk, rice husk, rice straw, spent mushroom compost, palm foliage, palm trunk, palm kernel shells, palm fiber, farm effluent, slaughterhouse waste, flower cuttings, spent flower compost, wheat straw, fruit waste, vegetable waste, and the like. Exemplary animal wastes include, but are not limited to, dead animals, animal feather, animal parts (such as animal intestines), and animal manure such as poultry manure, cow manure, goat manure, horse manure, sheep manure, and swine manure. Mill effluent may be, for example, palm oil mill effluent (POME) and POME sludge.

The organic waste to be treated in the disclosed process may be selected based on criteria such as availability due to for example geographical or seasonal variability, cost, suitability, desired product and product properties, and the like. For example, in palm oil producing regions, about 8 million tons of empty fruit bunch (EFB) are generated annually, and hence provides an abundant source of organic waste that can be treated using the disclosed process to at least partly convert the EFB into useful organic fertilizer. Similarly, a typical food processing plant can generate between about 1.5 to about 2 tons of sludge per day while a poultry slaughterhouse can generate about 300 m cu/day of wastewater, which result in abundant sources of organic waste for use in the disclosed process.

A single type of organic waste may be used in the disclosed process, or any combination of more than one type of organic waste may be used. For example, EFB may be used together with chicken manure, or food waste may be used together with POME sludge. Other exemplary combinations of organic wastes include, but are not limited to, a combination of chicken manure with dead chickens, a combination of chicken manure with chicken feathers, a combination of EFB with chicken manure, a combination of EFB with chicken manure and POME, and a combination of EFB and POME sludge.

Organic waste may be pre-processed prior to being used in the disclosed process. For example, a solid organic waste is typically pre-processed to obtain the desired particle size. Particle size is an important parameter in determining the efficacy of the treatment process. Particle size of organic waste for use in the disclosed process is preferably about 1 mm to about 20 mm, from about 2 mm to about 20 mm, from about 3 mm to about 20 mm, from about 4 mm to about 20 mm, from about 5 mm to about 20 mm, from about 6 mm to about 20 mm, from about 7 mm to about 20 mm, from about 8 mm to about 20 mm, from about 9 mm to about 20 mm, from about 10 mm to about 20 mm, from about 11 mm to about 20 mm, from about 12 mm to about 20 mm, from about 13 mm to about 20 mm, from about 14 mm to about 20 mm, from about 15 mm to about 20 mm, from about 16 mm to about 20 mm, from about 17 mm to about 20 mm, from about 18 mm to about 20 mm, from about 1 mm to about 19 mm, from about 1 mm to about 18 mm, from about 1 mm to about 17 mm, from about 1 mm to about 16 mm, from about 1 mm to about 15 mm, from about 1 mm to about 14 mm, from about 1 mm to about 13 mm, from about 1 mm to about 12 mm, from about 1 mm to about 11 mm, from about 1 mm to about 10 mm, from about 1 mm to about 9 mm, from about 1 mm to about 8 mm, from about 1 mm to about 7 mm, from about 1 mm to about 6 mm, from about 1 mm to about 5 mm, or from about 1 mm to about 4 mm, or from about 1 mm to about 3 mm. Most preferably, the particle size of the organic waste is from about 5 mm to about 10 mm.

Likewise, a liquid organic waste such as waste from food processing plants or slaughter houses may be pre-processed prior to being used in the disclosed process. Typically, the fatty and proteinaceous solid matters in such wastes are separated by a Dissolved Air Flotation (DAF) tank, after which the food particles are creamed off into a slurry tank leaving the DAF-treated liquid to be pumped into an aerator tank for further processing. Sludge from the DAF tank as well as the solid matters may be collected for use in the disclosed process.

Another typical pre-process step is to adjust the moisture content of the organic waste. This is because, the moisture content of organic waste varies widely depending on the source, and determines the availability of waste material that can be potentially converted to organic fertilizer. Preferably, the initial moisture of the organic waste is about 25% (wt) to about 70% (wt). For example, the initial moisture of the organic waste may be about 25% (wt) to about 70% (wt), about 25% (wt) to about 60% (wt), about 25% (wt) to about 50% (wt), about 25% (wt) to about 40% (wt), about 25% (wt) to about 35% (wt), about 25% (wt) to about 30% (wt), about 30% (wt) to about 70% (wt), about 40% (wt) to about 70% (wt), about 50% (wt) to about 70% (wt), about 60% (wt) to about 70% (wt), about 65% (wt) to about 70% (wt), about 30% (wt) to about 65% (wt), about 35% (wt) to about 60% (wt), about 40% (wt) to about 55% (wt), or about 45% (wt) to about 50% (wt). In one embodiment, the moisture content of the organic waste is about 30% (wt) to about 65% (wt). In another embodiment, the moisture content of the organic waste is about 35% (wt) to about 60% (wt). In yet another embodiment, the moisture content of the organic waste is about 50% (wt) to about 60% (wt).

Where the moisture content of the organic waste is not within the preferred ranges, the moisture content of organic waste may be adjusted so that it falls within the preferred ranges by means that are well known to those skilled in the art. For example, where the moisture content falls below the preferred ranges, the organic waste may be sprayed with water so that the moisture content is increased to a preferred level. Conversely, where the moisture content is above the preferred ranges, pre-drying may be applied to the organic waste to reduce the moisture content to the preferred level. Alternatively, the moisture content may be reduced by blending the organic waste with other organic wastes that are dry or that have lower moisture contents such as rice husk, rice straw, saw dust, and the like, to achieve the desired moisture content level.

Typically, the initial moisture content is maintained for at least about 4 h to about 10 h, at least about 5 h to about 10 h, at least about 6 h to about 10 h, at least about 7 h to about 10 h, at least about 8 h to about 10 h, at least about 9 h to about 10 h, at least about 4 h to about 9 h, at least about 4 h to about 8 h, at least about 4 h to about 7 h, at least about 4 h to about 6 h, or at least about 4 h to about 5 h from the start of the process. Thereafter, the moisture content is preferably reduced to about 10% (wt) to about 22% (wt), more preferably to about 13% (wt) to about 21% (wt), and most preferably to about 15% (wt) to about 20% (wt). For example, the moisture content may be reduced to about 10% (wt) to about 21% (wt), about 10% (wt) to about 20% (wt), about 10% (wt) to about 19% (wt), about 10% (wt) to about 18% (wt), about 10% (wt) to about 17% (wt), about 10% (wt) to about 16% (wt), about 10% (wt) to about 15% (wt), about 10% (wt) to about 14% (wt), about 10% (wt) to about 13% (wt), about 10% (wt) to about 12% (wt), about 10% (wt) to about 11% (wt), about 11% (wt) to about 22% (wt), about 12% (wt) to about 22% (wt), about 13% (wt) to about 22% (wt), about 14% (wt) to about 22% (wt), about 15% (wt) to about 22% (wt), about 16% (wt) to about 22% (wt), about 17% (wt) to about 22% (wt), about 18% (wt) to about 22% (wt), about 19% (wt) to about 22% (wt), about 20% (wt) to about 22% (wt), or about 21% (wt) to about 22% (wt). Advantageously, the reduced moisture content promotes efficient conversion of the organic waste to organic fertilizer by the microorganisms because some of the microorganisms are more effective in converting the organic waste at reduced moisture contents.

Typically, the organic waste is also heated to about 80° C. to about 175° C., about 90° C. to about 175° C., about 100° C. to about 175° C., about 110° C. to about 175° C., about 120° C. to about 175° C., about 130° C. to about 175° C., about 140° C. to about 175° C., about 150° C. to about 175° C., about 160° C. to about 175° C., about 170° C. to about 175° C., about 80° C. to about 170° C., about 80° C. to about 160° C., about 80° C. to about 150° C., about 80° C. to about 140° C., about 80° C. to about 130° C., about 80° C. to about 120° C., about 80° C. to about 110° C., about 80° C. to about 100° C., about 80° C. to about 90° C., about 90° C. to about 160° C., about 100° C. to about 150° C., about 110° C. to about 140° C., or about 120° C. to about 130° C. to remove unwanted microorganisms such as *Shigella* sp. microorganisms and *Salmonella* sp. microorganisms from the organic waste prior to being used in the disclosed process. Such unwanted microorganisms are not only harmful to human handling the product of the process but may also interfere with the conversion effected by the selected microorganisms in the disclosed composition.

After the heating pre-treatment, the organic waste or combination of more than one type of organic waste, may optionally be combined with other additives or nutrients to enhance conversion of the organic waste by the microorganisms or to increase the nutrient level of the organic fertilizer produced by the disclosed process. Such additives may be, for example, carbon sources such as ash, saw dust, dried leaves, wood shavings, and the like.

The organic waste, or mixture of organic wastes, is typically cooled to about 35° C. to about 75° C., about 40° C. to about 75° C., about 45° C. to about 75° C., about 50° C. to about 75° C., about 55° C. to about 75° C., about 60° C. to about 75° C., about 65° C. to about 75° C., about 70° C. to about 75° C., about 35° C. to about 70° C., about 35° C. to about 65° C., about 35° C. to about 60° C., about 35° C. to about 55° C., about 35° C. to about 50° C., about 35° C. to about 45° C., or about 35° C. to about 40° C. prior to seeding with the selected microorganisms. Preferably, the organic waste, or mixture of organic wastes, is cooled to about 50° C. to about 65° C., about 51° C. to about 65° C., about 52° C. to about 65° C., about 53° C. to about 65° C., about 54° C. to about 65° C., about 55° C. to about 65° C., about 56° C. to about 65° C., about 57° C. to about 65° C., about 58° C. to about 65° C., about 59° C. to about 65° C., about 60° C. to about 65° C., about 61° C. to about 65° C., about 62° C. to about 65° C., about 63° C. to about 65° C., about 64° C. to about 65° C., about 55° C. to about 64° C., about 55° C. to about 63° C., about 55° C. to about 62° C., about 55° C. to about 61° C., about 55° C. to about 60° C., about 55° C. to about 59° C., about 55° C. to about 58° C., about 55° C. to about 57° C., or about 55° C. to about 56° C. Once the organic waste, or mixture of organic wastes, is seeded with the selected microorganisms, the conditions within the treatment zone may be controlled and monitored so that the conditions may be maintained at an optimum required for enhancing conversion of the organic waste to organic fertilizer. The conditions to be monitored may include moisture, temperature, aeration, nutrient supply, and pH. The optimal values for such conditions typically depend on the selection of microorganisms in the microorganism composition.

In one embodiment, no pH control is applied and the process is allowed to proceed at the pH value of the organic waste(s) used. Typically, the pH of the organic waste is about 3 to about 10, about 4 to about 10, about 5 to about 10, about 6 to about 10, about 7 to about 10, about 8 to about 10, about 9 to about 10, about 3 to about 9, about 3 to about 8, about 3 to about 7, about 3 to about 6, about 3 to about 5, or about 3 to about 4. For example, the pH of EFB is about 6, the pH of citrus peels is about 4, and the pH of chicken manure is about 9.

In another embodiment, the pH is controlled at values of about 3 to about 10, about 4 to about 10, about 5 to about 10, about 6 to about 10, about 7 to about 10, about 8 to about 10, about 9 to about 10, about 3 to about 9, about 3 to about 8, about 3 to about 7, about 3 to about 6, about 3 to about 5, or about 3 to about 4. Control of pH may be applied, for example, by adding an appropriate pH buffer such as a phosphate buffer, an acetate buffer, a Tris buffer, and the like.

The microorganisms useful in the disclosed process are those that are capable of degrading carbon compounds or fixing nitrogen compounds. Advantageously, mixed cultures of the microorganisms are used in order to obtain a broad spectrum of degradation or fixation.

In one embodiment, there is provided a composition comprising at least one of *Bacillus* sp. microorganisms, *Pseudomonas* sp. microorganisms, *Bifidobacterium* sp. microorganisms, and *Lactobacillus* sp. microorganisms.

In another embodiment, there is provided a composition comprising one or more microorganisms from at least three of the following microorganism species: *Bacillus* sp. microorganisms, *Pseudomonas* sp. microorganisms, *Bifidobacterium* sp. microorganisms, and *Lactobacillus* sp. microorganisms.

In yet another embodiment, there is provided a composition comprising one or more microorganisms from each of the following microorganism species: *Bacillus* sp. microorganisms, *Pseudomonas* sp. microorganisms, *Bifidobacterium* sp. microorganisms, and *Lactobacillus* sp. microorganisms.

The *Bacillus* sp. microorganisms are preferably selected from the group consisting of *Bacillus pumilus, Bacillus stearothermophilus, Bacillus brevis, Bacillus cereus, Bacillus subtilis, Bacillus spheariues,* and *Bacillus licheniformis*. The *Pseudomonas* sp. microorganisms are preferably selected from the group consisting of *Pseudomonas alcaligenes* and *Pseudomonas marinoglutinosa*, the *Bifidobacterium* sp. is preferably *Bifidobacterium thermophilus*, and the *Lactobacillus* sp. microorganisms are preferably selected from the group consisting of *Lactobacillus casei, Lactobacillus planatarum,* and *Lactobacillus fermentus*.

The composition may further comprise one or more microorganisms selected from the group consisting of *Streptomyces* sp. microorganisms and *Corynebacterium* sp.

microorganisms. A preferred *Streptomyces* sp. microorganism is *Streptomyces pactum*, while a preferred *Corynebacterium* sp. microorganism is *Corynebacterium striatum*.

The composition may comprise a single species of microorganisms, for example one of *Bacillus* sp. microorganisms, *Pseudomonas* sp. microorganisms, *Bifidobacterium* sp. microorganisms, or *Lactobacillus* sp. microorganisms, with one or both of *Streptomyces* sp. microorganisms or *Corynebacterium* sp. microorganisms. Alternatively, the composition may comprise more than one species of microorganisms selected from *Bacillus* sp. microorganisms, *Pseudomonas* sp. microorganisms, *Bifidobacterium* sp. microorganisms, and *Lactobacillus* sp. microorganisms, with one or both of *Streptomyces* sp. microorganisms or *Corynebacterium* sp. microorganisms.

In another embodiment, the composition comprises at least two of *Bacillus* sp. microorganisms, *Pseudomonas* sp. microorganisms, *Bifidobacterium* sp. microorganisms, and *Lactobacillus* sp. microorganisms.

In another embodiment, the composition comprises at least three of *Bacillus* sp. microorganisms, *Pseudomonas* sp. microorganisms, *Bifidobacterium* sp. microorganisms, and *Lactobacillus* sp. microorganisms.

In a preferred embodiment, the composition comprises all four species of microorganisms: *Bacillus* sp. microorganisms, *Pseudomonas* sp. microorganisms, *Bifidobacterium* sp. microorganisms, and *Lactobacillus* sp. microorganisms, with one of *Streptomyces* sp. microorganisms or *Corynebacterium* sp. microorganisms. In a more preferred embodiment, the composition comprises all four species of microorganisms: *Bacillus* sp. microorganisms, *Pseudomonas* sp. microorganisms, *Bifidobacterium* sp. microorganisms, and *Lactobacillus* sp. microorganisms, with both of *Streptomyces* sp. microorganisms and *Corynebacterium* sp. microorganisms. In a most preferred embodiment, the composition comprises *Streptomyces pactum, Corynebacterium striatum, Bacillus pumilus, Bacillus stearothermophilus, Bacillus brevis, Bacillus cereus, Bacillus subtilis, Bacillus spheareius, Bacillus licheniformis, Pseudomonas alcaligenes, Pseudomonas marinoglutinosa, Bifidobacterium thermophilus, Lactobacillus casei, Lactobacillus planatarum* and *Lactobacillus fermentus*.

In another embodiment, the composition comprises one, two, three, four, or more microorganisms from *Bacillus* sp. microorganisms.

In another embodiment, the composition comprises one, two, three, four, or more microorganisms from *Pseudomonas* sp. microorganisms.

In one embodiment, the composition comprises one, two, three, four, or more microorganisms from *Bifidobacterium* sp. microorganisms.

In one embodiment, the composition comprises one, two, three, four, or more microorganisms from *Lactobacillus* sp. microorganisms.

In one embodiment, the composition comprises one, two, three, four, or more microorganisms from *Streptomyces* sp. microorganisms.

In one embodiment, the composition comprises one, two, three, four, or more microorganisms from *Corynebacterium* sp. microorganisms.

The selection of the microorganisms may be dependent on the type of organic waste that is to be treated.

The selected microorganisms may be combined with other additives to form the microorganism solution. The microorganism content of the microorganism solution may comprise about 5% (vol) to about 50% (vol) microorganisms, about 10% (vol) to about 50% (vol) microorganisms, about 15% (vol) to about 50% (vol) microorganisms, about 20% (vol) to about 50% (vol) microorganisms, about 25% (vol) to about 50% (vol) microorganisms, about 30% (vol) to about 50% (vol) microorganisms, about 35% (vol) to about 50% (vol) microorganisms, about 40% (vol) to about 50% (vol) microorganisms, about 45% (vol) to about 50% (vol) microorganisms, about 5% (vol) to about 40% (vol) microorganisms, about 5% (vol) to about 30% (vol) microorganisms, about 5% (vol) to about 20% (vol) microorganisms, or about 5% (vol) to about 15% (vol) microorganisms in a microorganism culture. In a preferred embodiment, the microorganism content of the microorganism solution comprises about 10% (vol) to about 20% (vol).

The microorganism solution may further comprise additives and nutrients for the microorganisms that are useful for promoting growth of the microorganisms and enhancing their degradation or nitrogen fixation activity on the organic waste to thereby enhance the efficacy and efficiency of the disclosed process. The additives may include biological catalysts (such as oxygenases and monooxygenases), buffers (such as phosphate buffer), diluents and surfactants (such as sorbitan, polysorbates, sorbitan esters and polyxamers). Examples of nutrients typically included in the microorganism solution to enhance microbial growth and degradation activity include carbohydrates (such as glucose, fructose, maltose, sucrose, and starch); other carbon sources (such as mannitol, sorbitol and glycerol); nitrogen sources (such as urea, ammonium salts, amino acids or crude proteins, yeast extract, peptone, casein hydrolysates and rice bran extracts); and inorganic compounds (such as magnesium sulfate, sodium phosphate, potassium phosphate, sodium chloride, calcium chloride and ammonium nitrate).

The microorganism solution is preferably kept cool under refrigeration until just before application to the organic waste. In some embodiments, the microorganism solution may be kept at room temperature (i.e. at about 25° C.) for up to about 4 hours.

Alternatively, the microorganisms may be recovered by centrifugation, mixed with a protective agent or fillers such as calcium carbonate, corn grits, corn flour, defatted rice bran, wheat bran, skim milk powder, and the like, and then freeze-dried in vacuo. The resulting powder of the microorganisms can be re-suspended, mixed or dissolved in a suitable solvent prior to use. Advantageously, the powder form of dry microorganisms is more stable, and can withstand long periods of storage and facilitates handling and transport. The microorganism powder can further be processed into pellets or granules.

The microorganism powder may contain from about $1 \times 10^{10}$ viable microorganisms per gram of powder to about $15 \times 10^{10}$ viable microorganisms per gram of powder, from about $1 \times 10^{10}$ viable microorganisms per gram of powder to about $14 \times 10^{10}$ viable microorganisms per gram of powder, from about $1 \times 10^{10}$ viable microorganisms per gram of powder to about $13 \times 10^{10}$ viable microorganisms per gram of powder, from about $1 \times 10^{10}$ viable microorganisms per gram of powder to about $12 \times 10^{10}$ viable microorganisms per gram of powder, from about $1 \times 10^{10}$ viable microorganisms per gram of powder to about $11 \times 10^{10}$ viable microorganisms per gram of powder, from about $1 \times 10^{10}$ viable microorganisms per gram of powder to about $10 \times 10^{10}$ viable microorganisms per gram of powder, from about $1 \times 10^{10}$ viable microorganisms per gram of powder to about $9 \times 10^{10}$ viable microorganisms per gram of powder, from about $1 \times 10^{10}$ viable microorganisms per gram of powder to about $8 \times 10^{10}$ viable microorganisms per gram of powder, from about $1 \times 10^{10}$ viable microorganisms per gram of powder to about $7 \times 10^{10}$ viable microorganisms per gram of powder, from about $1\times10^{10}$ viable microorganisms per gram of powder to about $6\times10^{10}$ viable microorganisms per gram of powder, from about $1\times10^{10}$ viable microorganisms per gram of powder to about $5\times10^{10}$ viable microorganisms per gram of powder, from about $1\times10^{10}$ viable microorganisms per gram of powder to about $4\times10^{10}$ viable microorganisms per gram of powder, from about $1\times10^{10}$ viable microorganisms per gram of powder to about $3\times10^{10}$ viable microorganisms per gram of powder, from about $1\times10^{10}$ viable microorganisms per gram of powder to about $2\times10^{10}$ viable microorganisms per gram of powder, from about $2\times10^{10}$ viable microorganisms per gram of powder to about $15\times10^{10}$ viable microorganisms per gram of powder, from about $3\times10^{10}$ viable microorganisms per gram of powder to about $15\times10^{10}$ viable microorganisms per gram of powder, from about $4\times10^{10}$ viable microorganisms per gram of powder to about $15\times10^{10}$ viable microorganisms per gram of powder, from about $5\times10^{10}$ viable microorganisms per gram of powder to about $15\times10^{10}$ viable microorganisms per gram of powder, from about $6\times10^{10}$ viable microorganisms per gram of powder to about $15\times10^{10}$ viable microorganisms per gram of powder, from about $7\times10^{10}$ viable microorganisms per gram of powder to about $15\times10^{10}$ viable microorganisms per gram of powder, from about $8\times10^{10}$ viable microorganisms per gram of powder to about $15\times10^{10}$ viable microorganisms per gram of powder, from about $9\times10^{10}$ viable microorganisms per gram of powder to about $15\times10^{10}$ viable microorganisms per gram of powder, from about $10\times10^{10}$ viable microorganisms per gram of powder to about $15\times10^{10}$ viable microorganisms per gram of powder, from about $11\times10^{10}$ viable microorganisms per gram of powder to about $15\times10^{10}$ viable microorganisms per gram of powder, from about $12\times10^{10}$ viable microorganisms per gram of powder to about $15\times10^{10}$ viable microorganisms per gram of powder, from about $13\times10^{10}$ viable microorganisms per gram of powder to about $15\times10^{10}$ viable microorganisms per gram of powder, or from about $14\times10^{10}$ viable microorganisms per gram of powder to about $15\times10^{10}$ viable microorganisms per gram of powder. In one embodiment, the microorganism powder contains from about $2\times10^{10}$ viable microorganisms per gram of powder to about $6\times10^{10}$ viable microorganisms per gram of powder.

Upon application to the organic waste, the mixture of organic waste and microorganisms is treated for about 0.5 h to about 4 h, about 1 h to about 4 h, about 1.5 h to about 4 h, about 2 h to about 4 h, about 2.5 h to about 4 h, about 3 h to about 4 h, about 3.5 h to about 4 h, about 0.5 h to about 3.5 h, about 0.5 h to about 3 h, about 0.5 h to about 2.5 h, about 0.5 h to about 2 h, about 0.5 h to about 1.5 h, or about 0.5 h to about 1 h. In one embodiment, the mixture is treated for about 2 h.

The process may further comprise the step of aerating the organic waste, for example by pumping in air from air compressors during the treatment. The air may be provided continuously during the treatment, or may, be provided periodically according to a pre-determined regime. For example, the air may be pumped in for about 10 min to about 30 min, about 10 min to about 20 min, about 10 to about 15 min, about 15 min to about 30 min, or about 20 min to about 30 min, stopped for about to 10 min to 30 min, about 10 min to about 20 min, about 10 min to about 15 min, about 15 min to about 30 min, or about 20 to about 30 min, and pumped in again for about 10 min to about 30 min, about 10 min to about 20 min, about 10 min to about 15 min, about 15 min to about 30 min, or about 20 to about 30 min. In one embodiment, the air is pumped in for about 10 min, stopped for about 20 min, and pumped in again for about 10 min.

The process may be allowed to proceed for a period of time until the level of the compounds to be degraded or converted reaches the target level. For example, the process may be allowed to proceed until the NPK value reaches the target level of about 5 to about 12, about 6 to about 12, about 7 to about 12, about 8 to about 12, about 9 to about 12, about 10 to about 12, about 11 to about 12, about 5 to about 11, about 5 to about 10, about 5 to about 9, about 5 to about 8, about 5 to about 7, or about 5 to about 6. Advantageously, a higher NPK value results in a more effective fertilizer in that a lesser amount of fertilizer is required to be used to promote plant growth compared to a fertilizer having a lower NPK value. An organic fertilizer with a higher NPK value is therefore more cost-effective than an organic fertilizer with a lower NPK value.

Alternatively, or simultaneously, the process may be allowed to proceed until the C:N ratio of the organic waste is reduced to a suitable range for use as organic fertilizer. Prior to conversion into fertilizer, the C:N ratio of an organic waste is typically high and unsuitable for use as fertilizer to promote plant growth. As the conversion process reaches maturity, the C:N ratio may be reduced from about 80:1 to about 20:1 depending on the organic waste(s) used as raw material. Preferably, the C:N ratio is reduced to a range of about 5:1 to about 30:1, about 6:1 to about 30:1, about 7:1 to about 30:1, about 8:1 to about 30:1, 9:1 to about 30:1, about 10:1 to about 30:1, about 11:1 to about 30:1, about 12:1 to about 30:1, about 13:1 to about 30:1, about 14:1 to about 30:1, about 15:1 to about 30:1, about 16:1 to about 30:1, about 17:1 to about 30:1, about 18:1 to about 30:1, about 19:1 to about 30:1, about 20:1 to about 30:1, about 21:1 to about 30:1, about 22:1 to about 30:1, about 23:1 to about 30:1, about 24:1 to about 30:1, about 25:1 to about 30:1, about 26:1 to about 30:1, about 27:1 to about 30:1, about 28:1 to about 30:1, about 29:1 to about 30:1, about 5:1 to about 29:1, about 5:1 to about 28:1, about 5:1 to about 27:1, about 5:1 to about 26:1, about 5:1 to about 25:1, about 5:1 to about 24:1, about 5:1 to about 23:1, about 5:1 to about 22:1, about 5:1 to about 21:1, about 5:1 to about 20:1, about 5:1 to about 19:1, about 5:1 to about 18:1, about 5:1 to about 17:1, about 5:1 to about 16:1, about 5:1 to about 15:1, about 5:1 to about 14:1, about 5:1 to about 13:1, about 5:1 to about 12:1, about 5:1 to about 11:1, about 5:1 to about 10:1, about 5:1 to about 9:1, about 5:1 to about 8:1, about 5:1 to about 7:1, about 5:1 to about 6:1, about 10:1 to about 25:1, about 10:1 to about 20:1, about 10:1 to about 15:1, about 15:1 to about 25:1, about 15:1 to about 20:1, or about 20:1 to about 25:1. In one embodiment, the C:N ratio is reduced to a range of about 15:1 to about 20:1.

The treatment period required may depend on factors such as the initial NPK level and/or C:N ratio of the organic waste to be treated, the type and concentration of the microorganisms used, and the treatment conditions applied in the process. Typically, the treatment period is at least about 18 h. Hence, the treatment period may be for example about 18 h to about 30 h, about 19 h to about 30 h, about 20 h to about 30 h, about 21 h to about 30 h, about 22 h to about 30 h, about 23 h to about 30 h, about 24 h to about 30 h, about 25 h to about 30 h, about 26 h to about 30 h, about 27 h to about 30 h, about 28 h to about 30 h, about 29 h to about 30 h, about 18 h to about 29 h, about 18 h to about 28 h, about 18 h to about 27 h, about 18 h to about 26 h, about 18 h to about 25 h, about 18 h to about 24 h, about 18 h to about 23 h, about 18 h to about 22 h, about 18 h to about 21 h, about 18 h to about 20 h, or about 18 h to about 19 h. In one embodiment, the treatment period is about 22 h. Advantageously, the desired NPK value of about 5 to about 12 and the desired C:N ratio of about 5:1 to about 30:1 may be achieved in about 18 h to about 30 h.

Where the treatment period is prolonged, the process may comprise the step of dosing the organic waste with a microorganism solution. The microorganism solution may be one that has been prepared from a microorganism powder as described above. Advantageously, the dosing promotes maintenance of the microorganism population during the prolonged treatment periods.

In one embodiment, the dosing is undertaken in a dosing regime of applying microorganism solution to the organic waste about every 2 h to about every 5 h, about every 3 h to about every 5 h, about every 4 h to about every 5 h, about every 2 h to about every 4 h, or about every 2 h to about every 3 h. The dosing regime undertaken may be determined based on such factors as the treatment load, the type of organic waste to be treated, the concentration of compounds, in the organic waste to be degraded or converted, the time period within which treatment is to be completed and the concentration of the microorganisms in the solution.

After treatment of the organic waste, the treated organic waste product is typically left to cool for about 2 h to about 6 h, about 3 h to about 6 h, about 4 h to about 6 h, about 5 h to about 6 h, about 2 h to about 5 h, about 2 h to about 4 h, about 2 h to about 3 h, about 3 h to about 5 h, or about 3 h to about 4 h. Cooling may be effected by sparging air to the treated organic waste.

The cooled organic waste is then typically allowed to age for about 1 day to about 5 days, 2 days to about 5 days, 3 days to about 5 days, 4 days to about 5 days, about 1 day to about 4 days, about 1 day to about 3 days, or about 1 day to about 2 days, to form an organic fertilizer product prior to being packaged. In one embodiment, the cooled organic waste is allowed to age for 2 days.

In one embodiment, there is provided an organic fertilizer comprising an organic waste and a disclosed composition.

In one embodiment, there is provided a kit comprising a microorganism composition as defined above, and instructions for contacting the composition with an organic waste under conditions to at least partly convert the organic waste to organic fertilizer. The kit may further comprise one or more additives or nutrients as defined above to enhance the growth of the microorganisms in the composition. In one embodiment, one or more compositions of microorganisms may be provided in a kit.

The disclosed process may be conducted in a system as disclosed herein. The system may comprise stirring means for mixing an organic waste and a disclosed composition in a treatment zone. The stirring means preferably comprise at least two arms located at different heights along the longitudinal axis of the treatment zone, wherein the at least two arms of the stirring means extend radially from the center of the treatment zone. The arms of the stirring means may be of any shape or geometry that ensures that the organic waste and disclosed composition disposed at the bottom of the treatment zone are rapidly and well mixed with the organic waste and disclosed composition disposed at the top of the treatment zone, and that the mixture can achieve the desired temperature, moisture content and aeration level. For example, the arms may be curved, rectangular, square, U-shaped, inverted U-shaped, L-shaped, T-shaped, symmetrical, asymmetrical, flat, angled, helical, propeller-shaped, or notch-shaped.

The system may also comprise heating means for heating the organic waste in the pre-treatment step to decontaminate or remove unwanted microorganisms as described above. The heating means may be any heat source that is capable of heating the organic waste located in the treatment zone. The heating means may comprise one or more electrical heating elements, or one or more heat exchangers, through which, for example, heating oil is circulated. The heating means may also comprise electric or gas heaters, or jets or hot air which can be directed specifically at the treatment zone. The heating means may also be a waste heat source, a solar heat source or a geothermal heat source. Exemplary waste heat sources include flue gases from gas turbines in power plants and incinerators, process gases of chemical and metallurgical operations and waste heat from other industrial processes. Typically, the heating means is capable of heating the organic waste to about 80° C. to about 175° C., about 90° C. to about 175° C., about 100° C. to about 175° C., about 110° C. to about 175° C., about 120° C. to about 175° C., about 130° C. to about 175° C., about 140° C. to about 175° C., about 150° C. to about 175° C., about 160° C. to about 175° C., about 170° C. to about 175° C., 80° C. to about 170° C., 80° C. to about 160° C., 80° C. to about 150° C., 80° C. to about 140° C., 80° C. to about 130° C., 80° C. to about 120° C., 80° C. to about 110° C., 80° C. to about 100° C., or 80° C. to about 90° C.

The system may further comprise a cooling means to reduce the temperature of the organic waste after the pre-treatment heating step so as not to kill the microorganisms in the composition that is to be added to the organic waste to treat the organic waste. The cooling means may be a stream of cold nitrogen gas. Typically, the cooling means is capable of reducing the temperature of the organic waste to about 35° C. to about 75° C., about 40° C. to about 75° C., about 45° C. to about 75° C., about 50° C. to about 75° C., about 55° C. to about 75° C., about 60° C. to about 75° C., about 65° C. to about 75° C., about 70° C. to about 75° C., about 35° C. to about 70° C., about 35° C. to about 65° C., about 35° C. to about 60° C., about 35° C. to about 55° C., about 35° C. to about 50° C., about 35° C. to about 45° C., or about 35° C. to about 40° C.

Each system may further be equipped with a temperature control unit to maintain the treatment zone at the required treatment temperature; moisture control means for maintaining the moisture level of the organic waste at a suitable level for treatment of the organic waste; a dryer, typically an air dryer, to dry the organic waste prior to being mixed with the microorganisms to remove excess moisture from the organic waste and achieve a desirable moisture content; aeration means for aerating the treatment zone during treatment of the organic waste; a control unit for controlling the stirring means, heating means, temperature control unit, moisture control means or aeration means; and a grinder for reducing the organic waste to a suitable particle size. The ground particles may be passed through a sieve to separate out the particles having unsuitable sizes while retaining particles having the desirable sizes. The particles having the desirable particles sizes may be stored in an organic waste container prior to being channeled into the treatment zone by a feeder, which may be, for example, a conveyor belt.

The disclosed process, composition, kit and system may be used to produce organic fertilizer from organic waste, increase the NPK value of an organic fertilizer, reduce the C:N ratio of an organic waste, increase the potassium value of an organic fertilizer, reduce odour of an organic waste, prevent leaching of nutrients from organic waste, or reduce waste accumulation.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

DETAILED DESCRIPTION OF DRAWINGS

Figure 1:
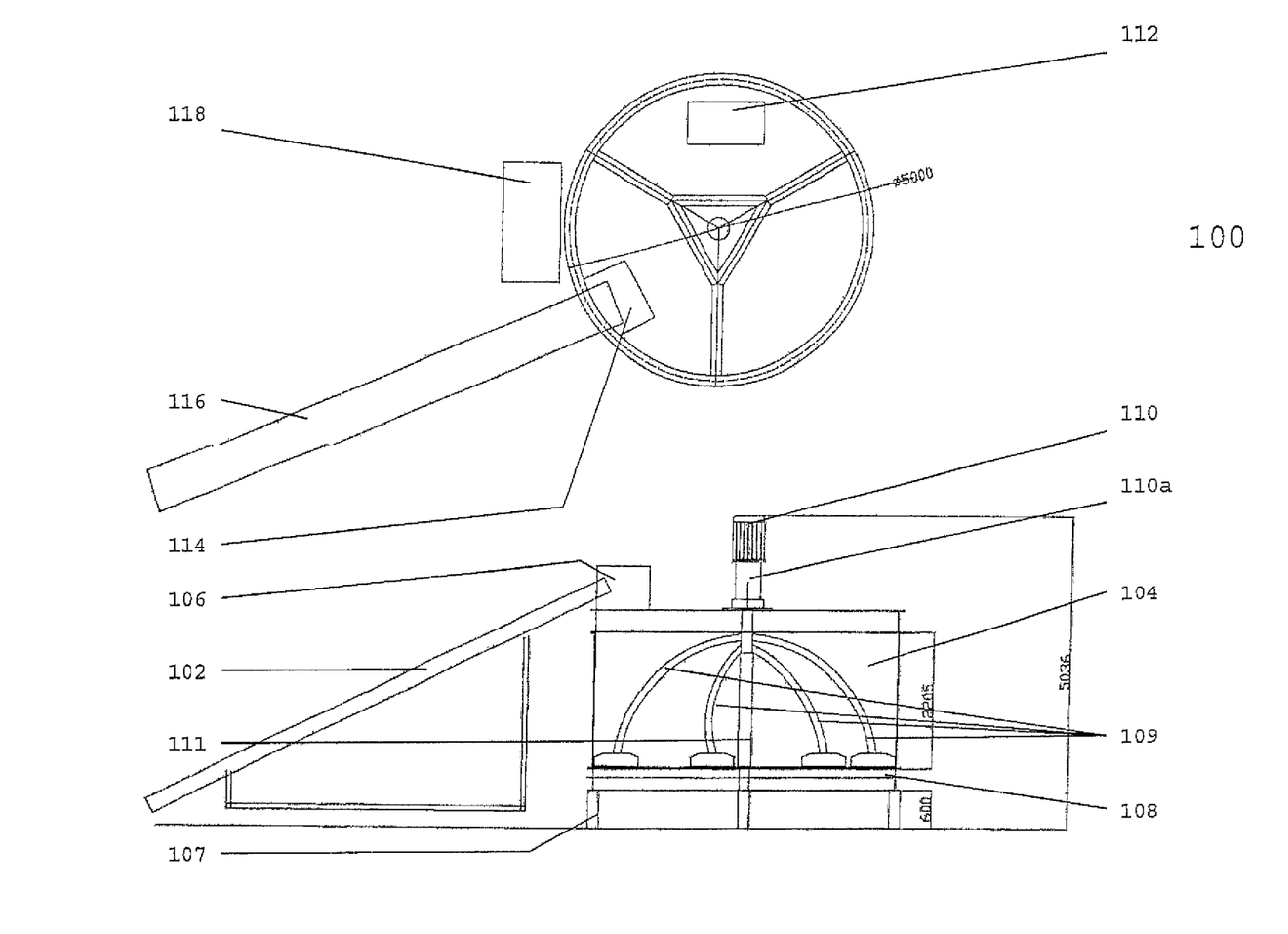
FIG. 1 shows a schematic diagram of a system for treating organic waste according to one disclosed embodiment.

Referring to FIG. 1, there is shown one embodiment of the disclosed system. In this embodiment, the system 100 comprises an input conveyor belt 102 for transporting an organic waste into a treatment zone 104 via an inlet 106. The treatment zone 104 is placed on a support 107, and is equipped with heating means 108 and stirring means 109. The stirring means 109 has four arms 109a, 109b, 109c and 109d, located at two different heights and extending radially from the longitudinal axis 111 of the treatment zone 104. The stirring means are controlled by a motor 110 and a decelerator 110a. The treatment zone 104 is covered by cover 112, which is equipped with an output conveyor belt 116 via outlet 114. A control unit 118 is also attached to the cover 112.

Once the organic waste is transported by the input conveyor belt 102 into the treatment zone 104 via inlet 106, the organic waste is heated to about 50° C. by the heating means 108, and a composition of selected microorganisms is added. The mixture of organic waste and microorganism composition is uniformly mixed by stirring means 109, the rate of stirring being controlled by the motor 110 and a decelerator 110a. The treatment of the organic waste is allowed to proceed for 2 h. The treated organic waste product is then removed from the treatment zone after 24 h by the output conveyor belt 116 via the outlet 114.

EXAMPLES (A) Preparation of Microorganism Composition

1 L of nutrient broth was prepared by mixing 10 g glucose, 8 g yeast extract and 5 g sodium chloride. The nutrient broth was then inoculated with the selected microorganisms: *Streptomyces pactum, Corynebacterium striatum, Bacillus pumilus, Bacillus stearothermophilus, Bacillus brevis, Bacillus, cereus, Bacillus subtilis, Bacillus spheareius, Bacillus licheniformis, Pseudomonas alcaligenes, Pseudomonas marinoglutinosa, Bifidobacterium thermophilus, Lactobacillus casei, Lactobacillus planatarum* and *Lactobacillus fermentus*. The nutrient broths inoculated with *Streptomyces pactum, Corynebacterium striatum, Bacillus pumilus, Bacillus brevis, Bacillus cereus, Bacillus spheareius, Pseudomonas alcaligenes, Pseudomonas marinoglutinosa, Lactobacillus casei, Lactobacillus planatarum* and *Lactobacillus fermentus* were cultured at 37° C., while the nutrient broths inoculated with *Bacillus stearothermophilus, Bacillus subtilis, Bacillus licheniformis*, and *Bifidobacterium thermophilus* were cultured at 60° C.

(B) Analytical Methods

NPK Values

Standard Kjeldahl's method (APHA 4500 $N_{org}$ B) was used to determine the total nitrogen content in the organic fertilizer. Standard acid digestion of the organic fertilizer followed by inductively coupled plasma atomic emission spectroscopy (ICP-AES) was used to determine the phosphorus and potassium contents in the organic fertilizer.

C:N Ratio

The organic carbon content was determined using the standard Loss on Ignition (LOI) method. A sample of the organic waste or organic fertilizer was weighed and its initial weight recorded. The sample was then placed in an oven at 350° C. for 3 hr. The sample was then cooled, re-weighed, and its final weight recorded. The organic carbon content was determined as follows:

% Organic Carbon=(Loss in weight÷Initial Weight)× 100

The nitrogen content was determined using standard Kjeldahl's method (APHA 4500 $N_{org}$ B).

The C:N ratio was then determined as follows:

C:N Ratio=% Organic Carbon:% Nitrogen

Example 1

Preparation of Organic Fertilizer from Raw Chicken Manure

Raw chicken manure, dead chicken and chicken feathers were mixed with saw dust, ash, rice husks, rice straw, wheat straw, spent mushroom compost or corn cobs. The initial moisture content of the organic waste mixture was adjusted to 35-60% (wt) for the first 6 h, and re-adjusted to and maintained at 15-20% (wt) thereafter. The mixture was heated to 100-150° C. for the first 2 h, after which the mixture was cooled to 50-65° C. The microorganism composition as prepared above was added to the mixture.

After mixing the mixture and microorganism for 2 h, air was pumped in for 10 min, stopped for 20 min, and resumed for another 10 min to maintain an aerobic environment. The process was allowed to run for 22 h, and then cooled. Air was pumped into the mixture for 3-4 h, after which the treated organic waste was allowed to age for 2 days. The NPK values and C:N ratios were determined using the analytical methods set out above.

Example 1(a)

| Raw Material | % wt |
| --- | --- |
| Raw chicken manure | 70 |
| Wood chips | 20 |
| Ash | 10 |

The NPK value of the organic fertilizer produced using the raw material composition in Example 1(a) was 6.

The C:N ratio of the raw material composition in Example 1(a) before treatment was 45:1. This was reduced to 20:1 after the 24 h treatment process.

Example 1(b)

| Raw Material | % wt |
| --- | --- |
| Raw chicken manure | 60 |
| Wood chips | 10 |
| Ash | 30 |

The NPK value of the organic fertilizer produced using the raw material composition in Example 1(b) was 9.

The C:N ratio of the raw material composition in Example 1(b) before treatment. was 40:1. This was reduced to 19:1 after the 24 h treatment process.

Example 1(c)

| Raw Material | % wt |
| --- | --- |
| Raw chicken manure | 50 |
| Wood chips | 30 |
| Ash | 20 |

The NPK value of the organic fertilizer produced using the raw material composition in Example 1(c) was 6.

The C:N ratio of the raw material composition in Example 1(c) before treatment was 50:1. This was reduced to 22:1 after the 24 h treatment process.

Example 1(d)

| Raw Material | % wt |
| --- | --- |
| Raw chicken manure | 40 |
| Dead chicken | 20 |
| Wood chips | 20 |
| Ash | 20 |

The NPK value of the organic fertilizer produced using the raw material composition in Example 1(d) was 9.

The C:N ratio of the raw material composition in Example 1(d) before treatment was 42:1. This was reduced to 21:1 after the 24 h treatment process.

Example 1(e)

| Raw Material | % wt |
| --- | --- |
| Raw chicken manure | 40 |
| Chicken feathers | 20 |
| Wood chips | 20 |
| Ash | 20 |

The NPK value of the organic fertilizer produced using the raw material composition in Example 1(e) was 9.

The C:N ratio of the raw material composition in Example 1(e) before treatment was 43:1. This was reduced to 20:1 after the 24 h treatment process.

Example 1(f)

| Raw Material | % wt |
| --- | --- |
| Raw chicken manure | 10 |
| Chicken feathers | 50 |
| Wood chips | 20 |
| Ash | 20 |

The NPK value of the organic fertilizer produced using the raw material composition in Example 1(f) was 9.

The C:N ratio of the raw material composition in Example 1(f) before treatment was 42:1. This was reduced to 20:1 after the 24 h treatment process.

As can be seen from the above Examples 1(a) to 1(f), treatment of the organic waste compositions in Examples 1(a) to 1(f) all resulted in organic fertilizers with high NPK values of at least 6. The organic waste compositions in Examples 1(b), 1(d), 1(e) and 1(f), in particular, resulted in organic fertilizers having higher NPK values of 9. Similarly, the initial C:N ratios of the organic waste compositions in Examples 1(a) to 1(f) ranging from 40:1 to 50:1 were all efficiently reduced to 19:1 to 22:1 after just 24 h.

Example 2

Preparation of Organic Fertilizer from Empty Fruit Bunch

Threshed EFP particles of 5-10 mm were mixed with chicken droppings, dead chickens, goat dung, POME, EFB ash and/or ash. The initial moisture content of the organic waste mixture was adjusted to 35-60% (wt) for the first 6 h, and re-adjusted to and maintained at 15-20% (wt) thereafter. The mixture was heated to 100-150° C. for the first 2 h, after which the mixture was cooled to 50-65° C. The microorganism composition as prepared above was added to the mixture.

After mixing the mixture and microorganism composition for 2 h, air was pumped in for 10 min, stopped for 20 min, and resumed for another 10 min to maintain an aerobic environment. The process was allowed to run for 22 h, and then cooled. Air was pumped into the mixture for 3-4 h, after which the treated organic waste was allowed to age for 2 days. The NPK values and C:N ratios were determined using the analytical methods set out above.

Example 2(a)

| Raw Material | % wt |
| --- | --- |
| EFB (threshed) | 70 |
| Raw chicken manure | 20 |
| Ash | 10 |

The NPK value of the organic fertilizer produced using the raw material composition in Example 2(a) was 6.

The C:N ratio of the raw material composition in Example 2(a) before treatment was 75:1. This was reduced to 27:1 after the 24 h treatment process.

Example 2(b)

| Raw Material | % wt |
| --- | --- |
| EFB (threshed) | 60 |
| Raw chicken manure | 20 |
| EFB ash | 20 |

The NPK value of the organic fertilizer produced using the raw material composition in Example 2(b) was 9.

The C:N ratio of the raw material composition in Example 2(b) before treatment was 70:1. This was reduced to 25:1 after the 24 h treatment process.

Example 2(c)

| Raw Material | % wt |
| --- | --- |
| EFB (threshed) | 50 |
| Raw chicken manure | 20 |

-continued

| Raw Material | % wt |
|---|---|
| EFB ash | 10 |
| POME | 20 |

The NPK value of the organic fertilizer produced using the raw material composition in Example 2(c) was 6.

The C:N ratio of the raw material composition in Example 2(c) before treatment was 65:1. This was reduced to 23:1 after the 24 h treatment process.

Example 2(d)

| Raw Material | % wt |
|---|---|
| EFB (threshed) | 80 |
| POME sludge | 20 |

The NPK value of the organic fertilizer produced using the raw material composition in Example 2(d) was 4.

The C:N ratio of the raw material composition in Example 2(d) before treatment was 85:1. This was reduced to 30:1 after the 24 h treatment process.

Example 2(e)

| Raw Material | % wt |
|---|---|
| EFB (threshed) | 50 |
| POME sludge | 50 |

The NPK value of the organic fertilizer produced using the raw material composition in Example 2(e) was 6.

The C:N ratio of the raw material composition in Example 2(e) before treatment was 73:1. This was reduced to 24:1 after the 24 h treatment process.

Example 2(f)

| Raw Material | % wt |
|---|---|
| EFB (threshed) | 50 |
| POME sludge | 30 |
| Ash | 20 |

The NPK value of the organic fertilizer produced using the raw material composition in Example 2(f) was 7.

The C:N ratio of the raw material composition in Example 2(f) before treatment was 70:1. This was reduced to 24:1 after the 24 h treatment process.

As can be seen from the above Examples 2(a) to 2(f), the organic waste composition in Example 2(a) to Example 2(f) resulted in organic fertilizers having NPK values of between 4 to 9. The organic waste composition in Example 2(b), in particular, resulted in an organic fertilizer with a high NPK value of 9. Similarly, the initial C:N ratios of the organic waste compositions in Examples 2(a) to 2(f) ranging from 65:1 to 85:1 were all efficiently reduced to 23:1 to 30:1 after just 24 h.

Example 3

Preparation of Organic Fertilizer from Food Waste Sludge

Food waste slurry and/or materials collected at the coarse screen station of a food processing plant were mixed with rice husks, rice straw, wheat straw, corn cobs, coffee bean husk, oil palm EFB, olive husk, fruit peels, wood chips, discarded vegetable, spent mushroom compost, spent orchid compost and/or flower cuttings. The initial moisture content of the organic waste mixture was adjusted to 35-60% (wt) for the first 6 h, and re-adjusted to and maintained at 15-20% (wt) thereafter. The mixture was heated to 100-150° C. for the first 2 h, after which the mixture was cooled to 50-65° C. The microorganism composition as prepared above was added to the mixture.

After mixing the mixture and microorganism composition for 2 h, air was pumped in for 10 min, stopped for 20 min, and resumed for another 10 min to maintain an aerobic environment. The process was allowed to run for 22 h, and then cooled. Air was pumped into the mixture for 3-4 h, after which the treated organic waste was allowed to age for 2 days. The NPK values and C:N ratios were determined using the analytical methods set out above.

Example 3(a)

| Raw Material | % wt |
|---|---|
| Food waste sludge | 50 |
| Saw dust | 25 |
| Ash | 25 |

The NPK value of the organic fertilizer produced using the raw material composition in Example 3(a) was 6.

The C:N ratio of the raw material composition in Example 3(a) before treatment was 60:1. This was reduced to 22:1 after the 24 h treatment process.

Example 3(b)

| Raw Material | % wt |
|---|---|
| Food waste sludge | 70 |
| Saw dust | 15 |
| Ash | 15 |

The NPK value of the organic fertilizer produced using the raw material composition in Example 3(b) was 9.

The C:N ratio of the raw material composition in Example 3(b) before treatment was 50:1. This was reduced to 19:1 after the 24 h treatment process.

Example 3(c)

| Raw Material | % wt |
|---|---|
| Food waste sludge | 60 |
| Saw dust | 10 |
| Ash | 30 |

The NPK value of the organic fertilizer produced using the raw material composition in Example 3(c) was 9.

The C:N ratio of the raw material composition in Example 3(c) before treatment was 45:1. This was reduced to 18:1 after the 24 h treatment process.

As can be seen from the above Examples 3(a) to 3(c), treatment of the organic waste compositions in Examples 3(a) to 3(c) all resulted in organic fertilizers with high NPK values of at least 6. The organic waste compositions in Examples 3(b) and 3(c), in particular, resulted in organic fertilizers having higher NPK values of 9. Similarly, the initial C:N ratios of the organic waste compositions in Examples 3(a) to 3(c) ranging from 45:1 to 60:1 were all efficiently reduced to 18:1 to 22:1 after just 24 h.

APPLICATIONS

Advantageously, the disclosed process for treating organic waste provides an improved process for producing organic fertilizer. More advantageously, the disclosed process substantially reduces the time required to produce organic fertilizers from several months as required using conventional composting methods to only one day or several days using the disclosed process, composition and system. Organic wastes having high C:N ratios may be rapidly converted to organic fertilizers with reduced C:N ratios after just 24 hours using the disclosed process, composition and system. This results in substantial reduction in energy and labour costs.

Advantageously, the disclosed process, composition and system substantially reduces, or completely eliminates, the foul odour of organic waste, to result in an organic fertilizer that is odourless.

Advantageously, the disclosed process for producing organic fertilizer from organic waste results in more effective organic fertilizers having increased NPK values.

Advantageously, the disclosed process also provides a solution to the waste disposal problem by converting organic waste into useful organic fertilizers.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A process for treating organic waste, the process comprising the step of contacting an organic waste having a moisture content ranging from about 10% (wt) to about 22% (wt) with one or more microorganism species from each of at least three of the following microorganism groups presented in (i)-(iv):
   (i) *Bacillus* sp. microorganisms, selected from the group consisting of *Bacillus pumilus, Bacillus stearothermophilus, Bacillus brevis, Bacillus cereus, Bacillus subtilis, Bacillus spheareius* and *Bacillus licheniformis*;
   (ii) *Pseudomonas* sp. microorganisms, selected from the group consisting of *Pseudomonas alcaligenes* and *Pseudomonas marinoglutinosa*;
   (iii) *Bifidobacterium* sp. microorganisms, which is *Bifidobacterium thermophiles*; and
   (iv) *Lactobacillus* sp. microorganisms, selected from the group consisting of *Lactobacillus casei, Lactobacillus plantarum* and *Lactobacillus fermentus*; and wherein said contacting includes mixing the organic waste with the microorganisms under aerobic environment for 18 to 30 hours to convert said organic waste to organic fertilizer.

2. A process as claimed in claim 1, further comprising the step of contacting said organic waste with one or more microorganisms selected from the group consisting of *Streptomyces* sp. microorganisms, and *Corynebacterium* sp. microorganisms.

3. A process as claimed in claim 1, wherein said contacting further comprises the step of adding an additional composition comprising one or more microorganism species from each of at least three of the microorganism groups selected from *Bacillus* sp. microorganisms, *Pseudomonas* sp, microorganisms, *Bifidobacterium* sp. microorganisms, and *Lactobacillus* sp. microorganisms to said organic waste.

4. A process as claimed in claim 3, wherein said composition further comprises one or more microorganisms selected from the group consisting of *Streptomyces* sp. microorganisms and *Corynebacterium* sp. microorganisms.

5. A process as claimed in claim 4, wherein the *Streptomyces* sp. is *Steptomyces pactum* and the *Corynebacterium* sp, is *Corynebacterium striatum*.

6. A process as claimed in claim 1, further comprising heating said organic waste to a temperature of 80° C. to 175° C. prior to said contacting step, to remove unwanted microorganisms from said organic waste.

7. A process as claimed in claim 6, further comprising the step of cooling said organic waste to a temperature of 35° C. to 75° C. prior to said contacting step.

8. A process as claimed in claim 3, wherein said composition is a solution.

9. A process as claimed in claim 3, wherein said composition is a powder.

10. A process as claimed in claim 8, wherein the microorganism content of said solution comprises 5% (vol) to 50% (vol) microorganisms in a microorganism culture.

11. A process as claimed in claim 9, wherein the microorganism content of said powder comprises $1 \times 10^{10}$ viable microorganisms per gram of powder to $15 \times 10^{10}$ viable microorganisms per gram of powder.

12. A process as claimed in claim 3, wherein the microorganisms of said microorganism composition are one or more microorganisms selected from the group consisting of *Streptomyces partum, Corynebacterium striatum, Bacillus pumilus, Bacillus stearothermophilus, Bacillus brevis, Bacillus cereus, Bacillus subtilis, Bacillus spheareius, Bacillus licheniformis, Pseudomonas alcaligenes, Pseudomonas marinogiutinosa, Bifidobacterium thermophiles, Lactobacillus easel, Lactobacillus plantarum* and *Lactobacillus fermentus*.

13. A process as claimed in claim 1, wherein said organic waste is selected from the group consisting of agricultural waste, food waste, organic refuse, mill effluent, municipal waste, sewage, sludge, animal waste, and industrial waste.

14. A process as claimed in claim 13, wherein said agricultural waste is selected from the group consisting of oil palm empty fruit bunch, olive husk, corn cob, coffee bean husk, rice husk, rice straw, spent mushroom compost, palm foliage, palm trunk, palm kernel shells, palm fiber, farm effluent, slaughterhouse waste, flower cuttings, spent flower compost, wheat straw, fruit waste, and vegetable waste.

15. A process as claimed in claim 13, wherein said animal waste is selected from the group consisting of poultry manure, cow manure, goat manure, horse manure, sheep manure, and swine manure.

16. A process as claimed in claim 1, wherein said organic waste has a particle size of 1 mm to 20 mm.

17. A process as claimed in claim 1, further comprising adding one or more additives or nutrients to said organic waste to enhance conversion of said organic waste by said microorganisms.

18. A method of using one or more microorganism species from each of at least three of the following microorganism groups presented in (i)-(iv):
  (i) *Bacillus* sp, microorganisms, selected from the group consisting of *Bacillus pumilus, Bacillus stearothennophilus, Bacillus brevis, Bacillus cereus, Bacillus subtilis, Bacillus spheariues* and *Bacillus licheniformis;*
  (ii) *Pseudomonas* sp, microorganisms, selected from the group consisting of *Pseudomonas alcaligenes* and *Pseudomonas marinogiutinosa;*
  (iii) *Bifidobacterium* sp. microorganisms, which is *Bifidobacterium thermophiles*; and
  (iv) *Lactobacillus* sp, microorganisms, selected from the group consisting of *Lactobacillus casei, Lactobacillus plantarum* and *Lactobacillus fermentus;*
  the method comprising:
  adjusting an initial moisture content of an organic waste between about 25% (wt) and about 70% (wt);
  adjusting a subsequent moisture content of said organic waste between about 10% (wt) to about 22% (wt)
  heating said organic waste to a temperature of 80°C. to 175°C. to remove unwanted microorganisms from said organic waste;
  cooling said organic waste to a temperature of 35°C. to 75° C.; and
  contacting said organic waste with the one or more microorganism species under aerobic environment for 18 to 30 hours for treating said organic waste to produce organic fertilizer, increase the NPK value of an organic fertilizer, increase the potassium value of an organic fertilizer, reduce odour of an organic waste, prevent leaching of nutrients from organic waste, or reduce waste accumulation.

19. The method as claimed in claim 18, further comprising contacting the organic waste with microorganisms selected from the group consisting of *Streptomyces* sp, microorganisms and *Corynebacterium* sp. microorganisms.

20. The method as claimed in claim 19, wherein said microorganism is selected from the group consisting of *Streptomyces pactum* and *Corynebacterium striatum*.

* * * * *

UNITED STATES PATENT AND TRADEMARK OFFICE
CERTIFICATE OF CORRECTION

PATENT NO. : 9,932,275 B2  
APPLICATION NO. : 14/269822  
DATED : April 3, 2018  
INVENTOR(S) : Chum Mok Puah et al.

Page 1 of 1

It is certified that error appears in the above-identified patent and that said Letters Patent is hereby corrected as shown below:

In the Claims

At Column 22, Claim number 3, Line number 15, "sp," should read -- sp. --.

At Column 22, Claim number 5, Line number 23, "sp," should read -- sp. --.

At Column 22, Claim number 12, Line number 50, the word "easel," should read -- casei --.

At Column 23, Claim number 18, Line number 10, "sp," should read -- sp. --.

At Column 23, Claim number 18, Line number 11, the word "stearothennophilus" should read -- stearothermophilus --.

At Column 23, Claim number 18, Line number 14, "sp," should read -- sp. --.

At Column 23, Claim number 18, Line number 16, the word "marinogiutinosa" should read -- marinoglutinosa --.

At Column 23, Claim number 18, Line number 18, the word "thermophiles" should read -- thermophilus --.

At Column 23, Claim number 18, Line number 19, "sp," should read -- sp. --.

At Column 24, Claim number 19, Line number 18, "sp," should read -- sp. --.

Signed and Sealed this  
Third Day of July, 2018

Andrei Iancu  
*Director of the United States Patent and Trademark Office*